United States Patent [19]

Nakamura et al.

[11] Patent Number: 5,401,635
[45] Date of Patent: Mar. 28, 1995

[54] NUCLEIC ACIDS ENCODING HUMAN PROHIBITIN MUTANTS AND DETECTION THEREOF

[75] Inventors: Yusuke Nakamura; Takaaki Sato, both of Tokyo, Japan

[73] Assignees: Cancer Institute; Eisai Co., Ltd., both of Tokyo, Japan

[21] Appl. No.: 114,461

[22] Filed: Aug. 31, 1993

Related U.S. Application Data

[62] Division of Ser. No. 9,255, Jan. 22, 1993.

[30] Foreign Application Priority Data

Jan. 24, 1992 [JP] Japan .................................. 4-011156
Nov. 18, 1992 [JP] Japan .................................. 4-308654

[51] Int. Cl.$^6$ ........................ C12Q 1/68; C12P 19/34;
C07H 21/04
[52] U.S. Cl. ...................................... 435/6; 435/91.2;
435/240.2; 536/23.1; 536/23.5; 536/23.51;
536/24.33
[58] Field of Search ........................ 435/240.2, 6, 91.2;
536/23.5, 23.51, 23.1, 24.33

[56] References Cited

PUBLICATIONS

White et al., *Genomics* 11,228–230 (1991).
Sato et al., *Cancer Research* 52, 1643–1646 (Mar. 16, 1992).
Adams et al., *Nature* 355, 632–634 (Feb. 13, 1992).
Nuell et al., *Mol. Cell. Biol.* 11(3), 1372–1381 (Mar. 1991).
Lundwall, *Bioch. Biophys. Res. Comm.* 161(3), 1151–1159 (1989).

*Primary Examiner*—Margaret Parr
*Assistant Examiner*—Kenneth R. Horlick
*Attorney, Agent, or Firm*—Flynn, Thiel, Boutell & Tanis

[57] ABSTRACT

A human prohibitin gene, a protein coded for by said gene, a gene analysis reagent to be used with them, and a quantitative determination of prohibitin in a biological sample by an immunological technique with the use of an antihuman prohibitin antibody and a method for analyzing a prohibitin gene of a human tissue for the occurrence of mutation by the PCR method with the use of oligonucleotides having partial base sequences of said gene as primers.

10 Claims, 3 Drawing Sheets

NUCLEIC ACIDS ENCODING HUMAN PROHIBITIN MUTANTS AND DETECTION THEREOF

This is a division of Ser. No. 08/009,255, filed Jan. 22, 1993 pending.

BACKGROUND OF THE INVENTION

1. Field of the Invention

The present invention relates to a human prohibitin, a gene coding for the same, an antibody against the human prohibitin and a gene analysis method wherein a part of the gene is used as a probe.

2. Description of the Related Art

It has been known for a long time that the mutation of cell genes plays an important role in cancer. Recent advances in genetic engineering have made it possible to amplify specific DNAs and to analyze gene mutations in cancer cells and thus contributed to the remarkable development in the field of investigations of cancer.

Analysis and identification on oncogenes, which are thought to participate in the malignant transformation of cells and the abnormal proliferation of cancer cells, are now in progress and the number of the oncogenes thus identified so far amounts to several multiples of ten. On the other hand, tumor suppressor genes having that operate functions against the functions shown by the oncogenes have been the focus of intense research interest in these several years. This is because it has been reported that fusion cells which are obtained by the fusion of cancer cells with normal cells would not show tumorigenic properties and would behave like normal ones, which suggests the existence of a gene capable of suppressing cancer in the normal cells.

Only about ten genes, including gene Rb of retinoblastoma [see Friend, S. H., et al., Proc. Natl. Acad. Sci., USA, 84, 9095 (1987)], gene p53 of colon cancer [see Lane, D. P., et al., Nature, 278, 261 (1979)] and gene WT of Wilms' tumor [see Call, K. M., et al., Cell, 60, 509 (1990)] have hitherto been proposed as candidates for tumor suppressor genes. In 1991, Nuell, M. J., et al. cloned a cDNA for a protein prohibitin having an antiproliferative activity from rat hepatocytes. Further, they reported that, when a synthetic mRNA of rat prohibitin was injected into fibroblasts and HeLa cells, it prevented the progress of the cell proliferation cycle into the S-stage and that the injection of a synthetic antisense oligo-nucleotide induced the progress into the S-stage [See Mol. Cell. Biol., 11, 1372 (1991)]. Thus, they suggested a possibility that it might be an antiproliferative factor.

However, a human prohibitin gene still remains wholly unknown and the clarification of the gene has been required for the clarification of the mechanism of the malignant transformation and proliferation of cells on the molecular level and, further, to conduct the diagnosis and treatment of cancer.

The present invention aims at providing a novel human prohibitin, a DNA coding for the same, and a reagent for gene analysis with the use of them.

DISCLOSURE OF THE INVENTION

Summary of the Invention

Under these circumstances, the present inventors obtained a PCR product of 444 bp by the reverse transcription polymerase chain reaction (RT-PCR) method by using a synthetic oligonucleotide containing a part of a rat prohibitin cDNA sequence as a primer and human hepatocyte mRNA as a template. By using the obtained PCR product as a probe in screening a cDNA library, they succeeded in the isolation of a human prohibitin gene. Results of analysis on the structure revealed that this gene was a DNA containing a novel human prohibitin cDNA consisting of 816 bases (the sequence ID No. 1) and coding for 272 amino acids (the sequence ID No. 1). Further, when a prohibitin gene of human breast cancer cell was analyzed, surprisingly several mutations were observed in the exon 4, which suggests that the gene of the present invention is a novel tumor suppressor gene. Thus, the present invention has been completed.

Accordingly, the present invention provides a human prohibitin having an amino acid sequence represented by the sequence ID No. 1, a peptide comprising or consisting a partial structure of the human prohibitin, a cDNA coding for the human prohibitin, a DNA represented by the sequence ID No. 1 which contains the cDNA coding for the human prohibitin, a part of the DNA, an intron DNA of a human prohibitin gene represented by the sequence ID No. 2 and a part of the intron DNA. The present invention also provides a method and a reagent for human prohibitin gene analysis wherein a part of the DNA sequence of the sequence ID No. 1 is used as a base sequence for a primer. The present invention further provides a protein which is an analogue of the human prohibitin, namely, a mutated prohibitin, a peptide comprising or consisting of a partial structure of the protein, a cDNA coding for the mutated prohibitin, a DNA relating to the human prohibitin and having a mutation, for example, a DNA confirmed in human breast cancer tissue, a part of the DNA, an intron DNA of the mutated human prohibitin gene and a part of the intron DNA. The mutants are also expected to be applicable in diagnosis of cancer. Furthermore, the present invention provides a host cell or host cells transformed by a plasmid or a vector having the cDNA of the present invention (that is, the cDNA coding for the human prohibitin or the cDNA coding for the mutated prohibitin) inserted therein, and an anti-prohibitin antibody against the human prohibitin or a partial structure fragment thereof, that is, a peptide comprising or consisting a partial structure of the human prohibitin, as an antigen. The present invention provides an amino acid sequence coding for human prohibitin and consisting of the amino acid sequence represented by the sequence ID No. 1, and a primer containing a DNA sequence consisting of a part of the DNA sequence represented by the sequence ID No. 1 and a primer containing a DNA sequence consisting of a part of the intron DNA sequence in the base sequence represented by the sequence ID No. 2.

The constitution of the present invention is as follows.

DETAILED DESCRIPTION OF THE INVENTION (1) Preparation of double-stranded DNA relating to RNA of human prohibitin Preparation of the gene coding for human prohibitin may be conducted as follows.

Namely, a messenger RNA (mRNA) is separated from a human organ, a complementary DNA (cDNA) is synthesized via the reverse transcription of the mRNA, and then a double-stranded DNA is synthesized.

The human prohibitin mRNA can be obtained from human tissues such as liver, heart and lung which are extirpated for some medical reasons. The RNA is extracted by, for example, the guanidine thiocyanate method [see Chirgwin, J. M., et al., Biochemistry, 18, 5294 (1979)] from human tissues. Then the RNA thus obtained is subjected to liquid chromatography by using an oligo(dT)cellulose column to thereby prepare the mRNA. By using the mRNA thus obtained as a template and oligonucleotides of two parts of the cDNA base sequence of rat prohibitin as primers, a single-stranded cDNA and then a double-stranded cDNA are synthesized with the use of a reverse transcriptase or the polymerase chain reaction (PCR) method in accordance with, for example, the method of Gubler, U., et al. [see Gene, 25, 263 (1983)] or the method of Frohman, A., et al. [see Proc. Natl. Acad. Sci., USA, 85, 8998 (1988)].

The double-stranded cDNA thus obtained is inserted into a plasmid or a phage by a well-known method. As examples of the vector into which the cDNA is to be inserted, pBluescript II SK, pBR322 and λgt11 may be cited, though any vector may be used therefor so long as it can be retained, replicated and amplified in the host cells. As an example of the method for inserting the cDNA into the plasmid, the method of Maniatis, J., et al. [see Molecular Cloning, A Laboratory Manual, Cold Spring Harbor Laboratory, p.239 (1982)] may be cited.

The plasmid or the phage vector thus obtained is then transfected into an appropriate host such as *Escherichia coli*. As examples of the *E. coli* strain usable as the host, E. coli HB101 and *E. coli* JM109 may be cited. When the vector of the cDNA is a plasmid, the vector can be retained in the host cells by the calcium chloride method or the calcium chloride/rubidium chloride method. When the vector of the cDNA is a phage, on the other hand, the vector can be retained in the host cells by, for example, the in vitro packaging method [see Molecular Cloning, Cold Spring Harbor Laboratory, p. 249 (1982)]. After the incubation and proliferation of the transformant, the recombinant DNA of the plasmid or the phage is isolated in accordance with a conventional method [see Molecular Cloning, Cold Spring Harbor Laboratory, New York (1982)] and digested with a restriction enzyme to analyze the base sequence of the cDNA. The base sequence is determined by the Maxam-Gilbert method [see Maxam, A. M., and Gilbert, W., Proc. Natl. Acad. Sci., USA, 74, 560 (1977)] or the dideoxy method [see Messing, J., et al., Nucl. Acids Res., 9, 309 (1981)].

(2) Confirmation of the full structure of human prohibitin gene

Since the cDNA obtained by the above-mentioned method does not code for the full length of the human prohibitin protein, the full structure of the human prohibitin gene is analyzed. by using human DNA libraries.

By using a human fetal brain cDNA library and a human chromosome library, a cDNA clone can be finished by the colony hybridization method [see Gene, 10, 63 (1980)] or the plaque hybridization method [see Science, 196, 180 (1977)] with the use of the RT-PCR product obtained by the above-mentioned method as a probe. The transformant thus cloned contains a cDNA which codes for the full amino acid sequence of human prohibitin or a partial amino acid sequence thereof. The base sequences of these cDNAs are analyzed by the same method as the one described above. If necessary, after a part of the cDNA, of which base sequence is determined, is synthesized and a cDNA is newly synthesized by the primer extension method [see Proc. Natl. Acad. Sci., USA, 76, 731 (1979)] with the use of the part of the cDNA as a primer, the cloning of the recombinant cDNA and the analysis of the base sequence thereof can be carried out in the same manner as the one described above. In order to clarify the structure of the chromosomal DNA of human prohibitin, a genomic clone is isolated by screening a human chromosome cosmid library with the use of the above-mentioned cDNA as a probe, and then the base sequences of these cDNAs are compared with those of the genomic clones the structures of which have been already determined. Thereby, the intron-exon junction can be analyzed.

Finally, the DNA containing the human prohibitin cDNA is determined as represented by the sequence ID No. 1 and the amino acid sequence of the human prohibitin is deduced as represented by the sequence ID No. 1. The sequence ID No. 2 represents the exon DNA of the exons 4 and 5 and the intron DNA around the exons 4 and 5. The human prohibitin consists of 272 amino acids and differs from rat prohibitin in the structure in one point, namely, the amino acid at 96 position in the former (man) is phenylalanine while the corresponding one in the latter (rat) is tyrosine.

(3) Human prohibitin recombinant expression vector and transformant thereof

The human prohibitin cDNA obtained by the above-mentioned method is inserted into an appropriate vector, which is then transfected into appropriate host cells to obtain a transformant. Then it is incubated in a conventional manner to obtain a large amount of human prohibitin from the culture.

A recombinant expression vector can be constructed by rejoining the cDNA coding for human prohibitin to the downstream of a promotor of a vector suitable for the expression of human prohibitin by a known method with the use of restriction enzymes and DNA ligase. Examples of the vector usable therefor include plasmids pBR322 and pUC18 originating in *E. coil*; a plasmid pUB110 originating in *Bacillus subtilis*; a plasmid pRB15 originating in a yeast; bacteriophages λgt10 and λgt11; and SV40, though any vector capable of replicating and amplifying in a host may be used therefor without restriction. Similarly, the promotor and the terminator are not particularly restricted so long as they are adapted for the host employed in the expression of the base sequence coding for human prohibitin, and any suitable combination may be selected therefor depending on the host to be used.

As the cDNA coding for human prohibitin, any DNA may be used so long as it codes for the human prohibitin protein. An artificial one obtained by chemical synthesis is also usable therefor.

Furthermore, the base sequence of the DNA (cDNA) is not restricted to the one represented by the sequence ID No. 1, so long as the protein thus expressed has the physiological activity of prohibitin. Namely, the DNA may have a base sequence which has undergone partial substitution, deletion, insertion or a combination thereof.

Then, the recombinant expression vector thus obtained is transfected into a host by, for example, the competent cell method [see J. Mol. Biol., 53, 154

(1970)], the protoplast method [see Proc. Natl. Acad. Sci., USA, 75, 1929 (1978)], the calcium phosphate method [see Science, 221, 551 (1983)], the in vitro packaging method [see Proc. Natl. Acad. Sci., USA, 72, 581 (1975)] or the virus vector method [see Cell, 37, 1053 (1984)] to thereby prepare a transformant. As the host, E. coli, Bacillus subtilis, yeasts or animal cells may be used. The transformant thus obtained is then incubated in an appropriate medium selected depending on the employed host. The incubation may be usually effected at a temperature of from 20° to 45° C. within a pH range of from 5 to 8 and, if necessary, under aeration and stirring. Human prohibitin may be separated and purified from the culture by appropriately combining well-known separation and purification methods. Examples of the methods include salting out, solvent precipitation, dialytic gel filtration, electrophoresis, ion exchange chromatography, affinity chromatography and reversed phase high performance liquid chromatography.

When injected into cells by the microinjection method, the human prohibitin thus obtained exhibits an activity of suppressing the proliferation of the cells.

(4) Preparation of antibody

The prohibitin to be used as the antigen may be one having a full structure, or a fragment or peptide having a partial structure thereof. Namely, a fragment or peptide part may be optionally selected from the full amino acid sequence of human prohibitin. The fragment or peptide may be prepared by the chemical synthesis method or the above gene recombination techniques or by degrading natural substances.

In order to prepare an antigen-carrier protein complex, various condensing agents, for example, glutaraldehyde, carbodiimide and maleimide activated esters may be used. The carrier protein may be those commonly employed in the art, such as bovine serum albumin, thyroglobulin or hemocyanin. In usual, a coupling method wherein the antigen and the carrier protein may be used at a ratio of from 1:1 to 1:5 is employed.

Examples of the animal to be immunized include mouse, rat, rabbit and guinea pig. The inoculation may be effected by subcutaneous, intramuscular or intraperitoneal administration. The antigen may be administered in the form of a mixture with complete Freund's adjuvant or incomplete Freund's adjuvant. The administration may be usually effected every two to five weeks.

A polyclonal antibody as an antihuman prohibitin antibody can be prepared by sampling the blood from an immunized animal and separating the serum. The antibody may be purified by any of the known methods. For example, it can be easily purified by any of the ammonium sulfate fractionation, PEG fractionation and ethanol fractionation methods, the use of an anion exchanger, or affinity chromatography.

A monoclonal antibody can be prepared by a well-known method. For example, antibody producing cells obtained from the spleen or lymph node of an immunized animal can be fused with myeloma cells and then isolated in the form of hybridomas. Myeloma cells originating in mouse, rat or man are usable and it is preferable to select ones having the same origin as that of the antibody producing cells, though hererogenous ones are available in some cases.

Cells can be fused in accordance with known methods, for example, the method of Köhler and Milsrein [see Nature, 256, 495 (1975)]. Examples of a fusion promoter include polyethylene glycol and Sendal virus. In usual, cells can be fused by reacting the antibody producing cells with the myeloma cells usually at a ratio in count of from 1:1 to 10:1 for about 1 to 10 minutes at a temperature of 20 to 40° C., preferably 30° to 37° C., in about 20 to 50% polyethylene glycol (average molecular weight: 1,000–4,000) solution.

Various immunochemical methods can be used in screening the antihuman prohibitin antibody producing hybridomas. Examples thereof include the ELISA (enzyme-linked immunosorbent assay) with the use of a microplate coated with human prohibitin and the EIA (enzyme immunoassay) with the use of a microplate coated with antiimmunoglobulin antibody. By using these immunochemical methods, wells which produce the desired antibody can be determined.

From these wells, a clone is obtained via cloning by, for example, the limiting dilution analysis. The hybridomas are usually screened and grown in a medium for animal cells (for example, RPMI 1640) containing 10 to 20% of calf fetal serum to which HAT (hypoxanthine, aminopterin and thymidine) have been added.

The clone thus obtained is transplanted into the peritoneal cavity of a BALB/C mouse to which pristane has been previously administered. After 10 to 14 days, the ascites rich in the monoclonal antibody is sampled to be used as a material from which the antibody is purified. Alternately, the culture obtained by incubating the clone can be used as a material for purifying the antibody. The monoclonal antibody may be recovered by the methods cited above for purifying immunoglobulin.

It is expected that the immunological assays with the use of these antibodies enable the identification and determination of human prohibitin in biological human samples and these antibodies are thus applicable as diagnostic agents for cancer.

The immunological determination of human prohibitin may be effected in accordance with any of well-known methods including the fluorescent antibody method, the passive agglutination method and the enzyme-labeled antibody technique. The monoclonal antibody of the present invention may be any of the classes IgG, IgA and IgM. Further, the Fab' or Fab fraction prepared by eliminating the Fc' or Fc region of this antibody, or a polymer thereof, may be used. Furthermore, a chimetic antibody thereof is also usable.

(5) Gene analysis of human cancer tissue

The analysis of the human prohibitin gene provided by the present invention for the occurrence of mutation can be conducted by appropriately selecting base sequences at suitable sites from the gene and using the synthetic oligonucleotides thereof as primers.

The human prohibitin gene is analogous in structure with the gene Cc [see Eveleth, D. D., et al., Nucleic Acids Res., 14, 6169 (1986)] and the gene NF1 [see Hall. A., Cell, 61, 921 (1990)]. As the selection sites for the primers, any site of the human prohibitin gene, for example, the cDNA part, the intron part or the junction of them, may be selected, but it is suitable to select the base sequence for the primer from a base sequence part where the structural analogy with the gene Cc is well preserved, namely, the exon 4 part or the intron parts located in front or rear of the exon 4 part. The oligonucleotide to be used as the primer may consist of from several to several tens of bases, preferably from 10 to 30 bases and still preferably from 15 to 25 bases.

As the biological sample to be subjected to the gene analysis, normal human tissues and various human cancer tissues may be employed. The DNA of the employed tissue may be extracted and prepared by, for example, the method of Sato, T., et al. [see Cancer Res., 50, 7184 (1990)].

The present inventors first conducted gene analysis on human breast Cancer cells. An Oligo-nucleotide having the base sequence, 5'-GTACTCCAGC-CTAGGCAAC-3', at the 134- to 152-positions in the sequence ID No.2, that is, in an intron part located in the exon 4 of the human prohibitin gene according to the present invention and another oligonucleotide having the antisense code, 5'-CAGGAAACTAGCAGC-CACAT-3', of the base sequence at the 491- to 510-positions in the sequence ID No.2, that is, in an intron part located in the exon 4 of the human prohibitin gene according to the present invention were used as the primers. Human breast cancer tissues (26 specimens) extirpated for some medical reasons were treated by the PCR method with the use of the above-mentioned two primers to amplify the desired human prohibitin gene. Then host cells, which were transformed by a plasmid having the human prohibitin gene inserted thereinto, were incubated by the same method as the one described above to thereby give clones. Mutation was observed as shown by the results of the base sequence analysis given in Table 1. The mutation includes those occurring in the exon 4 part, for example, a mutation of CGC at the codon 105 into CAC, namely, a mutation of arginine into histidine (specimen No. 342), a deletion of two bases in the codon 90-92 (specimen No. 120) and a mutation in the codon 88 (specimen No. 139).

These facts suggest that the human prohibitin gene of the present invention has a characteristic as a tumor suppressor gene and thus closely relates to the malignant transformation and proliferation of cells, thus providing a method for the diagnosis of human breast cancer.

According to the present invention, a novel human prohibitin and a cDNA coding for the same can be provided. Further, the present invention enables the qualitative and quantitative analysis of human prohibitin in a biological sample by an immunological technique with the use of an antihuman prohibitin antibody and the gene analysis of a biological sample by the PCR method with the use of some oligo-nucleotides having partial base sequence of the human prohibitin gene as primers. The antihuman prohibitin antibody and the oligonucleotide having partial base sequence of the human prohibitin gene are useful as clinical diagnostic reagents. Furthermore, there is a possibility that the human prohibitin would be applicable as medicines. Thus, it is useful as a reagent for investigations. In addition, the provision of a mutated human prohibitin gene in a human breast cancer tissue and a protein coded for thereby makes it possible to quantitatively determine the gene or the protein in a biological sample and thus a novel diagnostic method for human breast cancer might be provided. Based on the anticipated functions of prohibitin, these effects are not restricted to breast cancer.

EXAMPLES

Figure 1:
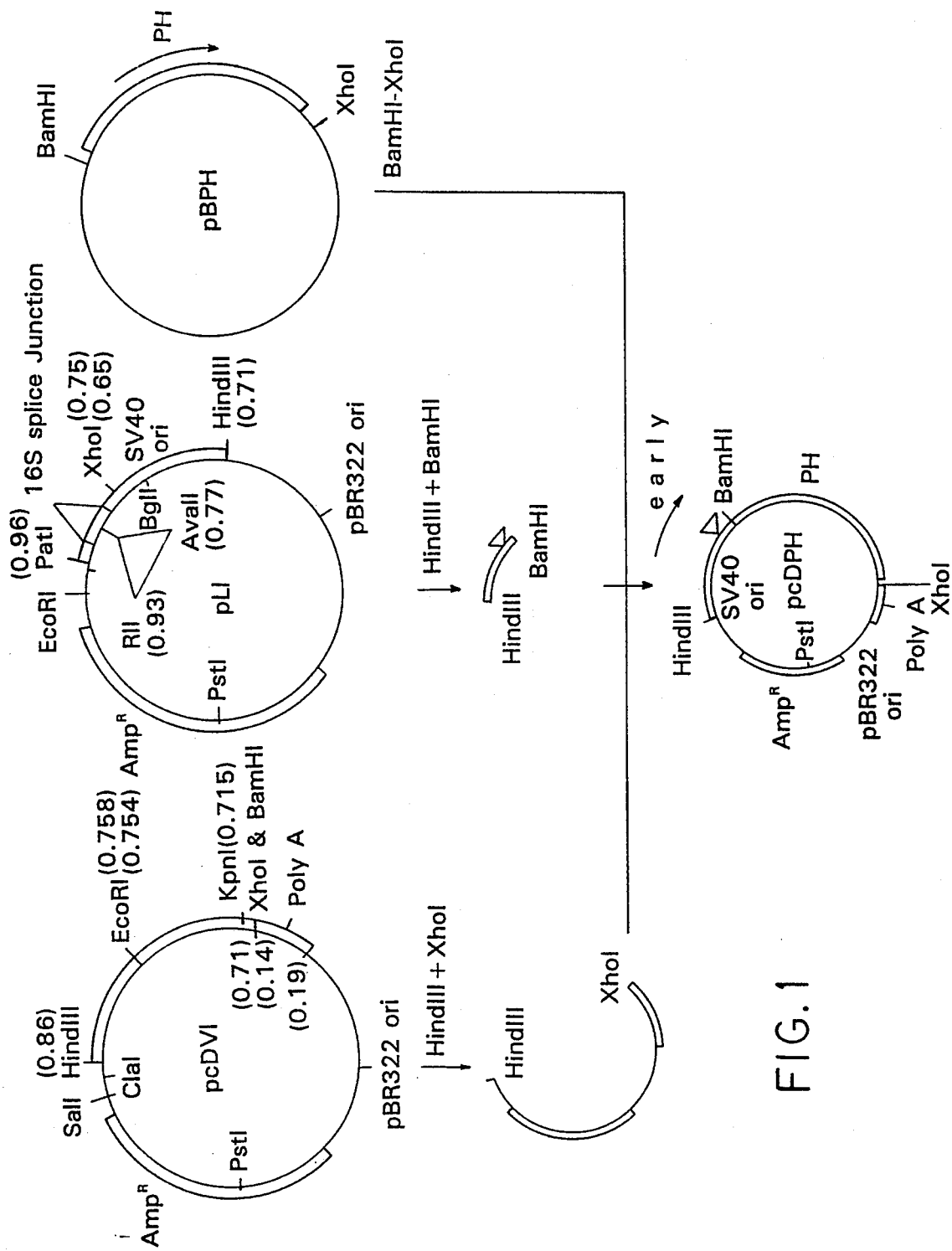
FIG. 1 shows a process for constructing pcDH by using vector pcD.

To further illustrate the present invention in greater detail, and not by way of limitation, the following Examples will be given.

Example 1

(1) Preparation of mRNA 1 g of a human liver extirpated for some medical reasons was suspended in 10 ml of a solution of 4M of guanidium thiocyanate, 0.5% of N-lauroylsarcosine sodium, 25 mM of sodium citrate (pH 7.0), 1M of mercaptoethanol and 0.1% of Antiform (Sigma) and then homogenized with Polytron. The obtained homogenate was superposed on a 5.7M aqueous solution of cesium chloride containing 0.1M of EDTA and centrifuged at 26,000 rpm at 25° C. for 36 hours by using an ultracentrifuge (SRP28 SA Rotor, Hitachi) to recover RNA in the form of pellets.

The RNA thus obtained was dissolved in a 10 mM Tris-HCl buffer solution (pH 7.4). After adding ethanol, the mixture was allowed to stand at −70° C. for 1 hour. Next, the mixture was centrifuged and the RNA thus precipitated was dissolved in a 10 mM Tris-HCl (pH 7.4). Then 0.5M KCl was further added thereto.

The obtained mixture was then poured into an oligo(dT)cellulose column (20 mm in diameter and 150 mm in height) equilibrated with the same buffer solution. After thoroughly washing with 0.5M KCl and 10 mM Tris-HCl, mRNA was eluted with a 10 mM aqueous solution of Tris-HCl.

500 μg of the mRNA originating in the human liver was then superposed on 15 ml of a sucrose solution of a concentration gradient of 10 to 28% containing 50 mM of Tris-HCl (PH 7.4), 0.2M of NaCl and 1 mM of EDTA and centrifuged at 26,000 rpm at 20° C. for 16 hours by using an ultracentrifuge (SRP 28 Rotor, Hitachi).

Next, the content in the centrifuging tube was fractionated into 500-μl portions from the bottom of the centrifuging tube and ethanol was added to each fraction to thereby precipitate the mRNA.

(2) Synthesis of partial human prohibitin cDNA

A partial human prohibitin cDNA was synthesized by the RT-PCR method. Primers for the RT-PCR method were prepared by the use of the base sequences within a region preserved between the rat prohibitin cDNA sequence reported by Nuell, M. J., et al. and the gene Cc of Drosophila:

right primer (3'):
   5'-TCACCCTCAGCAGAGATGAT-3'    (SEQ ID NO:3);

left primer (5'):
   5'-CGCTCTCGACCACGTAATGT-3'    (SEQ ID NO:4).

The method comprises combining 0.1 μg of the human liver mRNA, a PCR buffer, dNTPs, DTT and 25 pmol of the 3'-oligonucleotide primer together, incubating the mixture at 65° C. for 5 minutes, adding 40 units of RNA sin and 200 units of M-MLV-RT (moloney murine leukemia virus-reverse transcriptase: BRL) thereto, adjusting the total volume to 25 μl, incubating the mixture at 42° C. for 90 minutes, adding the PCR buffer, dNTPs, 75 pmol of the 3'-oligonucleotide primer and 100 pmol of the 5'-oligonucleotide primer to the reaction mixture to thereby adjust the total volume to 100 μl, and conducting the PCR.

The PCR conditions involves a cycle of annealing at 55° C. for 2 minutes, extension at 72° C. for 2 minutes and denaturation at 94° C. for 1 minute, which is repeated 35 times, to amplify the DNA, thereby obtaining a product of 444 bp.

(3) Insertion into pBSKII and transformation

The above RT-PCR product was electrophoresed on a 1.2% agarose gel to obtain a DNA fragment of 444 bp. This DNA fragment was subjected to terminal repair with Klenow enzyme and the terminal was phosphorylated with T4 ribonucleotide kinase. Then, the DNA fragment thus treated was ligated to pBluescript II SK (-), which had been cleaved with Eco RV and then treated with alkaline phosphatase, by using T4 ligase. The vector thus obtained was transfected into E. coli HB 101 to thereby transform the E. coli, and clones H1, H2, and H3 were selected in the obtained transformants. The base sequences of these clones were determined by the dideoxy method (Pharmacia AB, T7 sequencing kit). As a result, it was found out that the clone H3 had a high homology with rat prohibitin.

(4) Identification of human prohibitin cDNA clone

Preparation of probe:

The above clone H3 was cleaved with Bam H1 and Hind III and a DNA fragment of 444 bp was recovered from a 1.2% agarose gel. After introducing $\gamma$-$^{32}$P-CTP in a conventional manner with the use of Klenow enzyme, this DNA fragment was employed as a probe.

Identification of cDNA clone:

A filter (about $3.5 \times 10^5$ closes) was prepared by transferring phage DNAs from a fetal human brain cDNA library (CLONTECH) and screened by the DNA hybridization method with the use of the above-mentioned mentioned probe to obtain two positive clones. When the base sequences of these two cDNAs were determined, the same base sequence as that of H3 was found in one of them, thus confirming that the full DNA sequence corresponds to the DNA sequence containing the cDNA sequence coding for human prohibitin, as represented by the sequence ID No. 1.

E. coli HB101 pBPH transformed by pBluescript II SK (-) having this cDNA inserted therein was deposited with Fermentation Research Institute of the Agency of Industrial Science and Technology under the accession number FERM P-12714 on Jan. 21, 1992, and then changed to an internationally deposition under the accession number FERM BP-3808 on Mar. 26, 1992.

Identification of genomic clone:

A filter was prepared by transferring colony DNAs from a human genomic cosmid library prepared by a conventional method and screened by the DNA hybridization method with the use of the above-mentioned probe. As a result, four positive clones were obtained. When the base sequences of these four cosmid DNAs were determined by using a primer prepared based on the sequence of H3, it was confirmed that one of these clones involved a part of the same base sequence as that of H3. As the result of an analysis on intron-exon Junctions based on a comparison between this base sequence with the base sequence of cDNA, it was confirmed that exons were located in the following positions in the DNA base sequence of the sequence ID No. 1: exon 1 in the positions 1–23; exon 2 in the positions 24–138; exon 3 in the positions 139–300; exon 4 in the positions 301–443; exon 5 in the positions 444–560; exon 6 in the positions 561–656; and exon 7 in the positions 657–1020.

The sequence ID No. 2 shows the base sequence of the intron parts coupled with the exons 4 and 5 of the human prohibitin gene, wherein the amino acid numbers in the parts of the exons 4 and 5 are assigned in accordance with the sequence ID No. 1.

Example 2

Expression of cDNA in COS7 cells:

pcD vector [see Okayama, H., and P. Berg., Mol. Cell Biol., 3, 280 (1983)] has the DNA replication initiating point of a virus SV40 and an early promoter. When cDNA is inserted downstream of this promoter and then transfected into a cell strain COS7 [see Y. Glutzman, Cell, 23, 175 (1981)] producing T antigen of SV40, this recombinant plasmid is amplified and a transient and intense expression of cDNA occurs.

A Bam HI-Xho I fragment involving the whole coding region was excised from pBSPH which was a full-length cDNA clone and connected to a vector pcDV$_1$ [see F. Sanger et al., Proc. Natl. Acad. Sci., 74, 5463 (1977)] cleaved with Xho I+Hind III with DNA ligase to thereby give pcDPH (refer to FIG. 1).

By this operation, the cDNA was inserted downstream of the promoter in the correct orientation.

The plasmid DNA of pcDPH was prepared and transfected into cells COS7 by the DEAE-dextran method [see T. Yokota et al., Proc. Natl. Acad. Sci., 82, 68 (1985)]. The cells thus transformed produced human prohibitin in their cells after approximately one day.

Example 3

Expression of human prohibitin in mammalian cell strain:

The pcDPH obtained in the above Example 2 and pSV$_2$-dhfr [see S. Subramani, R. Mulligan, and P. Berg, Mol. Cell. Biol., 1, 854 (1981)] were co-transfected into cells BHK (ATCC, CRL 1632 tk− ts13, Dainippon Pharmaceutical Co., Ltd.) by the electropotation method (Bio-Rad Co., Gene Pulser 0.4 kV/0.4 cm, 500 μF, 10–15 msec., twice) or the calcium phosphate method (Pharmacia AB, Kit Cell Phect). By screening with 250 nM methotrexate (MTX), MTX-resistant clones were obtained.

These clones produced human prohibitin in their cells.

Further, pcDPH, pSV$_2$-dhfr and psV$_2$-neo [see P. J. Southern & P. Berg., J. Mol. Appl. Gent., 1, 327 (1982)] were co-transfected into cells CHO-K1 (ATCC CCL 61) by the calcium phosphate method [see Kao, F. T., and T. T. Puck, Proc. Natl. Acad. Sci., 60, 1275 (1981)]. By screening with 1 mg/ml of G-418, a neo-resistant clone was obtained. This clone was further incubated in a medium containing 5 μM of MTX to obtain a clone producing human prohibitin in its cells.

Example 4

Expression of human prohibitin by E. coli:

(1) Preparation of expression plasmid

Figure 2:
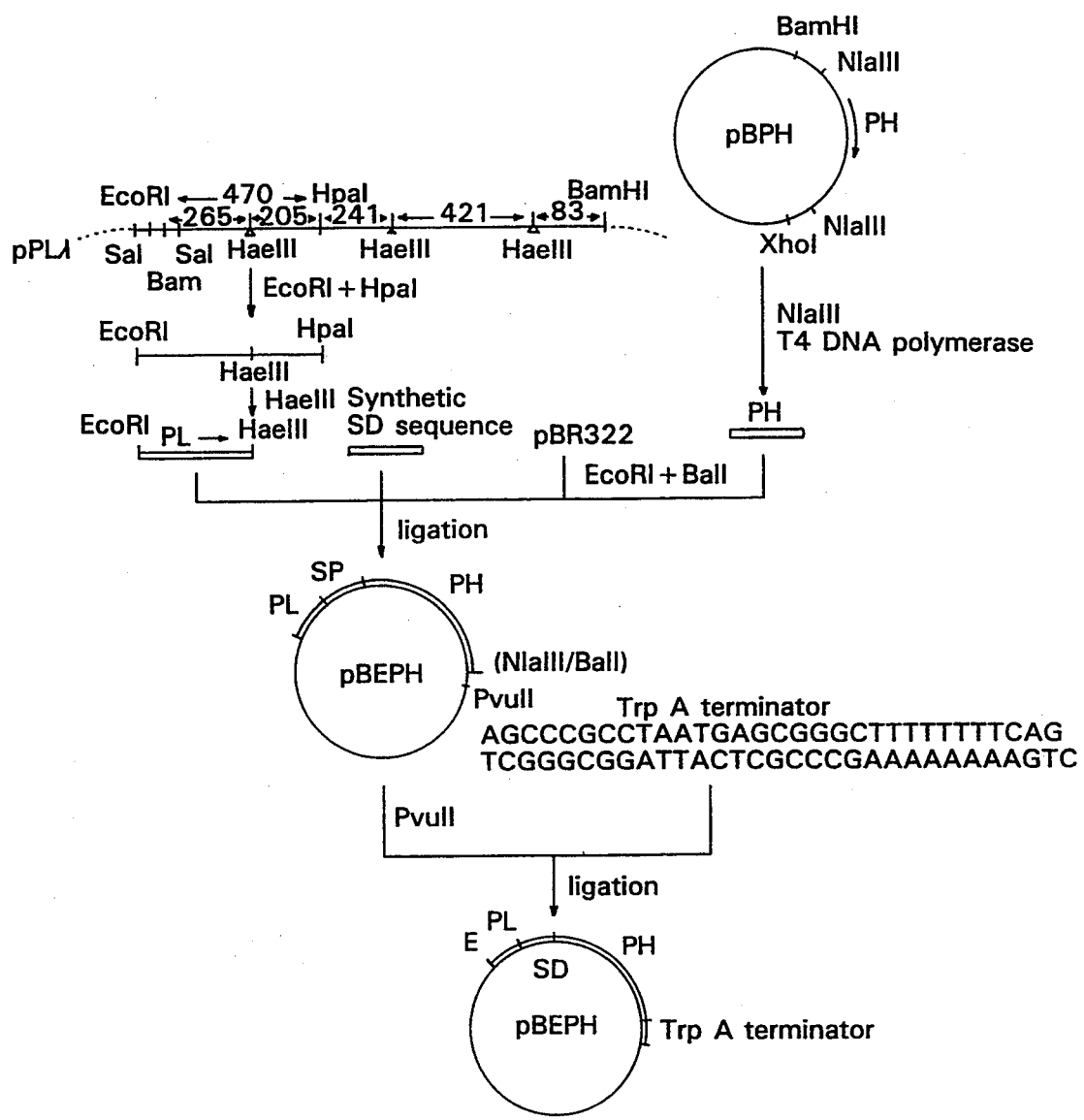
FIG. 2 shows a process for constructing pBEPH.

A DNA coding for the human prohibitin protein was prepared from pBPH and inserted between the promoter PL of λ phage and the terminator rrnB of E. coli to thereby construct an expression plasmid pBEPH (refer to FIG. 2).

pPL-λ (Pharmacia AB) involving the promoter PL of λ phage was cleaved with Eco RI and Hpa I to recover a fragment of 470 bp involving the promoter PL. Then it was cleaved with Hae III to recover a fragment of approximately 265 bp involving the promoter. This fragment and another DNA fragment of the following synthetic SD sequence:

5'-TTAACAACTAAGGGTATCGACAATG-(SEQ ID NO:5)

3'-AATTGTTGATTCCCATAGCTGTTAC-5'(SEQ ID NO:6)

were further ligated to pBR322, which was obtained by cleaving pBPH with Nla III, treating with T4 DNA polymerase, and then cleaving the human prohibitin cDNA fragment thus obtained with EcoR I and Bal I, to thereby give pBEPH.

Example 5

Figure 3:
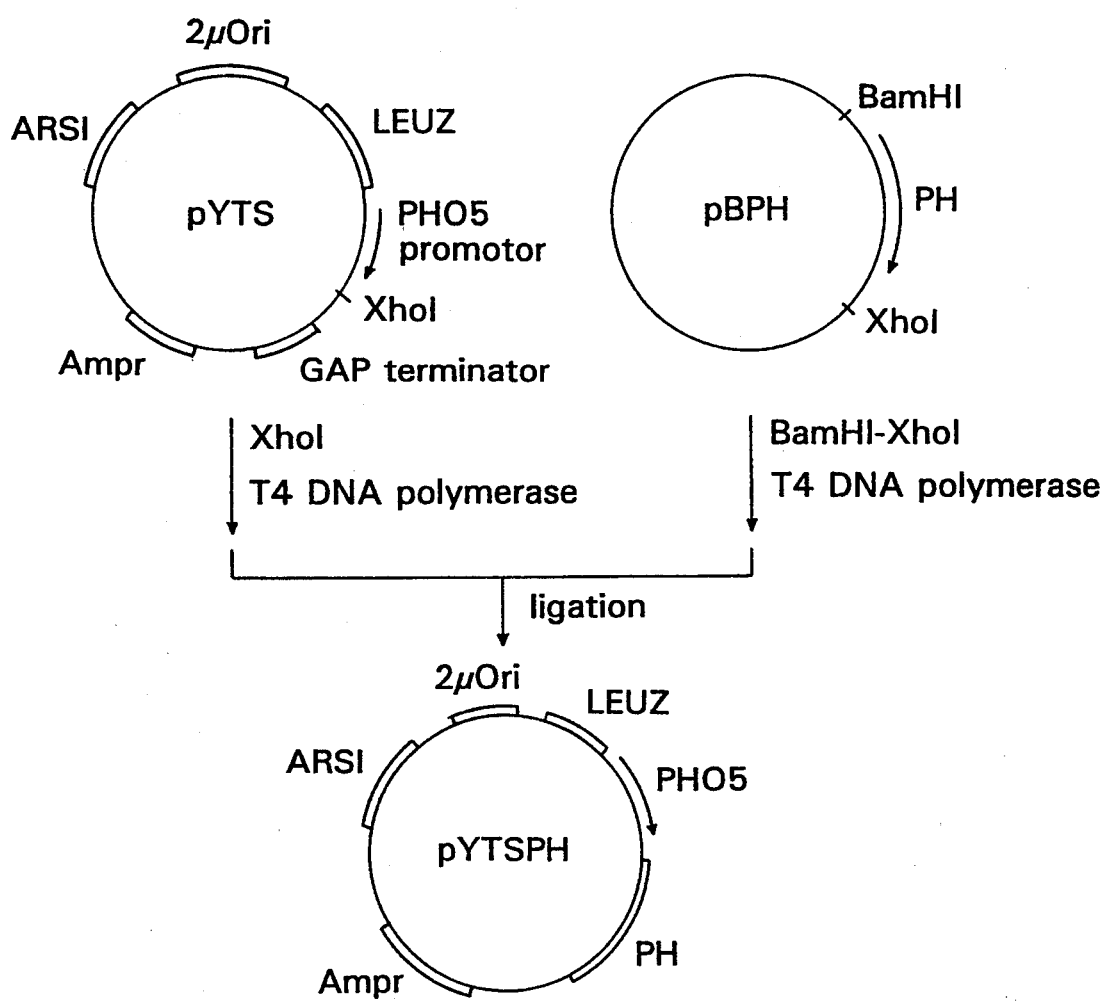
FIG. 3 shows a process for constructing pYTSPH.

Expression in yeast:

In order to construct an expression vector of human prohibitin in a yeast, a vector pYTS for heterogenic gene expression in yeasts was digested with a restriction enzyme Bam HI at its cloning site and the cleavage site was blunted with T4 DNA polymerase. The above pBPH was digested with restriction enzymes BamHI-XhoI to thereby obtain the human prohibitin gene part of the pBPH. The human prohibitin gene part thus obtained was separated and purified by using a low-melting agarose gel. After blunting the restriction enzyme cleavage sites with T4 DNA polymerase, the vector pYTS DNA treated with T4 DNA polymerase was ligated thereto with T4 DNA ligase, thus constructing pYTS-PH (refer to FIG. 3).

The plasmid pYTS-PH was transfected into Saccharomyces cerevisiae AH22 by the lithium acetate method [see Ito et al., J. Bacteriol., 153, 163 (1983)] for transformation to thereby obtain a clone carrying the pYTS-PH. The plasmid pYTS was a heterogenic gene expression vector of a sandwich structure having a promoter PH05, which was acid phosphatase capable of undergoing induced expression, and a terminator of GAP (glyceraldehyde-3-phosphate dehydrogenase), which was a transcription termination factor, in the downstream of the cloning site.

The expression of human prohibitin in the yeast S. cerevisiae AH22 carrying pYTS-PH was effected in the following manner. Namely, the clone was grown in 10 ml of a minimal medium of Burkholder et al. containing 20 μg/ml of histidine and 0.15% of KH$_2$PO$_4$ at 30° C. until the incubation reached a stationary phase. Then the clone was transplanted into 100 ml of Burkholder's medium containing 0.15% of KCl instead of 0.15% of KH$_2$PO$_4$ and the promoter PH05 was induced to express at 30° C. for 48 hours while control with phosphoric acid.

After carrying out the induced expression at 30° C. for 48 hours under controlling with phosphoric acid, the yeast was collected by centrifuging and suspended in 10 ml of a 1.2M sorbitol/50 mM KH$_2$PO$_4$-50 mM Na$_2$PO$_4$ buffer (pH 7.2). Then 100 μl of 500 μg/ml Zymolyae 100 T (Seikagaku) was added thereto and the yeast was lysed at 37° C. for 1 hour. After lysing the yeast, the cell pellets were dissolved in 1 mM PMSF-50 mM Tris-HCl (pH 7.5)-10 mM EDTA-1% SDS and centrifuged at 15,000 rpm for 30 minutes. Then a cell extract was collected from the supernatant and electrophoresed on SDS-PAGE. After staining with Coomassie Blue, human prohibitin produced in excess in the yeast could be detected at 30 KDa, which was the anticipated molecular weight. Further, it was confirmed that this protein was human prohibitin by the Western blotting technique with the use of a human prohibitin antibody.

Example 6

Analytical experiment on gene of breast cancer tissue:

(1) Method for extracting DNA from breast cancer tissue

In order to detect mutations in the human prohibitin gene in breast cancer, DNA was extracted from tumors and normal tissues of patients with breast cancer.

Breast cancer tissues extirpated for some medical reasons and normal tissues were frozen with liquid nitrogen and finely ground by using a mortar and a pestle while adding liquid nitrogen in portions to thereby give fine powder. Then the powder was transferred into a tube containing 4 ml of a solution (10 mM Tris-HCl, 50 mM NaCl, 50 mM EDTA, pH 8.5) while cooling with liquid nitrogen. After thorough stirring, 0.35 ml of protease K (10 mg/ml) and 0.4 ml of 10% SDS were added thereto and the mixture was allowed to stand at 37° C. for 4 hours or longer while occasionally stirring.

Next, 4 ml of a phenol/chloroform/isoamyl alcohol (25:24:1) mixture was added thereto and the obtained mixture was slowly stirred with a shaker at 37° C. overnight. After centrifuging at 3,000 rpm for 20 minutes, the supernatant was carefully transferred into a new tube with a Pasteur piper. Then 4 ml of a phenol/chloroform/isoamyl alcohol (25:24:1) mixture was added thereto and the obtained mixture was slowly stirred with a shaker at 37° C. for 2 hours. After centrifuging at 3,000 rpm for 20 minutes, the supernatant was transferred into a new tube. Then 4 ml of a chloroform/isoamyl alcohol (24:1) mixture was added thereto and the obtained mixture was slowly stirred with a shaker. After centrifuging at 8,000 rpm for 10 minutes, the supernatant was transferred into a new tube. The above procedure was repeated until no white denatured protein layer was observed in the intermediate layer.

Then an equivalent amount of isopropyl alcohol was added to the supernatant to thereby precipitate DNA. When white suspended matters (DNA) were precipitated, the precipitate was transferred into an Eppendorf tube with a siliconized Pasteur piper. When only a small amount of the precipitate was obtained, DNA was precipitated by centrifuging at 8,000 rpm for 10 minutes, the collected DNA was rinsed with 70% ethanol, the ethanol was discarded and then the residue was allowed to stand at room temperature for several hours to thereby evaporate the alcohol. Thus, the DNA was extracted and used in the analysis of the prohibitin gene.

(2) Analysis on mutations of prohibitin gene in breast cancer tissues

In order to detect mutations in the prohibitin gene in the breast cancer tissues, the base sequence of the exon 4 which was highly homologous with the gene Cc of Drosophila was determined.

First, it was necessary to amplify the exon 4 by the PCR method. As the result of the structural analysis on the human prohibitin cDNA of the present invention and the cosmid clone of chromosome human prohibitin, intron-exon junctions had been confirmed as shown in the sequence ID No. 2. Based on this sequence, two primers having the following base sequences, which were partial base sequences of two introns located in front and rear of the exon 4, were prepared as the primers for PCR:

5'-GTACTCCAGCCTAGGCAAC-3' (a sense code of bases at the positions 134–152 in the sequence ID No. 2); and 5'-CAGGAAACTAGCAGCCACAT-3' (an antisense code of bases at the positions 491–510 in the sequence ID No. 2).

With the use of these primers, a region involving the exon 4 was first amplified by the PCR method. The PCR product was treated with polynucleotide kinase and T4 DNA polymerase and then subcloned into the Eco RV site of pBluescript II SK (-) which had been pretreated with cIp. Subsequently, the reaction mixture was transfected into *E. coli* and a plasmid DNA was prepared. By using primers having base sequences of further inner parts compared with those of the primers employed in PCR (namely, a primer having a sense code part of bases at the positions 197–214 in the sequence ID No. 2 and another primer having an antisense code part of bases at the positions 421–437 in the sequence ID No. 2), the DNA base sequence of the plasmid DNA was determined in both the directions.

As a result of the comparison and examination on the base sequences of the exons 4 in the prohibitin chromosomes from the normal and cancer tissues, mutation was confirmed in tumor tissue specimens No. 136, No. 342, No. 120 and No. 218, as Table 1 shows.

TABLE 1

| Specimen no. | Age | LOH* | Codon | Mutation in base | Amino acid |
|---|---|---|---|---|---|
| 136 | 38 | + | 88 | GTC → GCC | Val → Ala |
| 342 | 60 | + | 105 | CGC → CAC | Arg → His |
| 120 | 35 | + | 90–92 | TCACACT → TCACT | Frame → shift |
| 218 | 39 | + |  | GTG/gtgagtgaaca → (SEQ ID NO: 2, position 397–410) | GTG/gtgagtgaata (SEQ ID NO: 7) |

*Loss of heterozygosity in the 17th chromosome.

In the cases of other exons, mutation can be detected in a similar manner by designing appropriate primers from the base sequence represented by the sequence ID No. 2. Further, abnormalities in the base sequence may be detected by using, for example, the RNase protection method or the SSCP method which are well known.

Example 7

Preparation of polyclonal antibody:

Based on the human prohibitin amino acid sequence described in the sequence ID No. 1, five peptides having amino acid sequences in the 69- to 87-positions, the 110- to 118-positions, the 140- to 158-positions, the 175- to 197-positions and the 200- to 221-positions were selected as antigens and each of these peptides was synthesized with the use of an automatic peptide solid phase synthesizer. Each of the obtained peptides was formulated into a complex with a carrier protein keyhole limpet by using a maleimide activated ester condensing agent to thereby give an immunogen. These complexes were mixed with the complete Freund's adjuvant and rabbits were subcutaneously immunized therewith at an interval of two weeks five times in total, to thereby prepare antibodies.

The production of an antibody was confirmed by conducting the ELISA which comprises immobilizing each antigen peptide to a microplate and adding the sampled serum and an antirabbit immunoglobulin antibody labeled with horse-radish peroxidase thereto.

The reactivities of these antibodies thus obtained against various samples were examined. First, each of these antibodies exhibited a reactivity against each of the antigen synthetic peptides in the above ELISA. Further, each of these antibodies exhibited a positive reaction in the Western blotting analysis wherein the human prohibitin expressed by incubating *E. coli* transformed by a plasmid containing human prohibitin cDNA was used.

Normal human tissues, human cancer tissues and human cancer cell strains were each homogenized with a 1% CHAPS phosphate solution and the extracted solution was analyzed by the Western blotting method. As a result, an antibody against a peptide having an amino acid sequence in the 200- to 221-positions described in the sequence ID No. 1 as an antigen exhibited positive reactions against normal human tissues of liver and submucosal nerve, a negative one against a submucosal nerve cancer tissue and a positive one against a cultured cancer cell strain (human breast cancer MX-1).

These results indicate that the antibody of the present invention is applicable to the confirmation and determination of prohibitin in biological samples.

What we claim is:

1. An isolated intron DNA fragment from a human prohibitin gene consisting of nucleotides 134 to 152 or 491 to 510 of SEQ ID NO: 2.

2. A method for human prohibitin gene analysis, comprising the steps of obtaining a human sample containing DNA; amplifying a prohibitin gene fragment of the DNA comprising exon 4 in a polymerase chanin reaction comprising said DNA, deoxynucleotide triphospates, polymerase, and a primer pair, wherein said primer pair consists of one primer targeted to each of the first two intron segments of SEQ ID NO: 2, said intron segments flanking said exon 4; and analyzing the amplified prohibitin gene fragment for the occurrence of mutation by nucleotide sequence determination, RNase protection assays, or single-strand conformation polymorphism assays.

3. The method for human prohibitin gene analysis as claimed in claim 2, wherein said primer is one of an oligonucleotide having a base sequence of the 134- to 152-positions in the base sequence SEQ ID NO: 2 and an oligonucleotide having the antisense code of the 491- to 510-positions in the base sequence SEQ ID NO:2.

4. A reagent for human prohibitin gene analysis for the occurrence of mutation, wherein said reagent is a primer selected from the group consisting of an oligonucleotide having the base sequence of the 134- to 152-positions in the base sequence SEQ ID NO: 2 and an oligonucleotide having an antisense code of the 491- to 510-positions in the base sequence SEQ ID NO: 2.

5. A cDNA having the sequence of SEQ ID NO: 1 except that codon GTC, the codon for valine, at the 88-amino acid position is GCC, the codon for alanine.

6. A cDNA having the sequence of SEQ ID NO: 1 except that codon CGC, the codon for arginine, at the 105-amino acid position is CAC, the codon for histidine.

7. A DNA having the sequence of SEQ ID NO: 1 except that a dinucleotide CA in CACAC at the 320- to 324-base positions is lacking.

8. A DNA having the sequence of SEQ ID NO: 2 except that the base C at the 409-base position is T.

9. A host cell transformed by a plasmid which can be expressed in the host cell and which plasmid has inserted therein the cDNA as claimed in claim 5.

10. A host cell transformed by a plasmid which can be expressed in the host cell and which plasmid has inserted therein the cDNA as claimed in claim 6.

* * * * *

UNITED STATES PATENT AND TRADEMARK OFFICE
CERTIFICATE OF CORRECTION

PATENT NO. : 5 401 635
DATED : March 28, 1995
INVENTOR(S) : Yusuke NAKAMURA et al It is certified that error appears in the above-indentified patent and that said Letters Patent is hereby corrected as shown below:

Column 21, Line 55; change "chanin" to ---chain---.

Signed and Sealed this

Fourteenth Day of November, 1995

Attest:

BRUCE LEHMAN

Attesting Officer    Commissioner of Patents and Trademarks

SEQUENCE LISTING ( 1 ) GENERAL INFORMATION:

( i i i ) NUMBER OF SEQUENCES: 8

( 2 ) INFORMATION FOR SEQ ID NO: 1:

( i ) SEQUENCE CHARACTERISTICS:
        ( A ) LENGTH: 1020 base pairs
        ( B ) TYPE: nucleic acid
        ( C ) STRANDEDNESS: double
        ( D ) TOPOLOGY: linear ( i i ) MOLECULE TYPE: cDNA to mRNA ( i i i ) HYPOTHETICAL: yes ( i v ) ANTI-SENSE: no (vi) ORIGINAL SOURCE:
  (A) ORGANISM: Homosapiens
  (C) INDIVIDUAL ISOLATE:
  (G) CELL TYPE:

(vii) IMMEDIATE SOURCE:
  (A) LIBRARY: Human fetal brain cDNA library
  (B) CLONE:

(ix) FEATURE:
  (A) NAME/KEY: Peptide
  (B) LOCATION: 23 to 839
  (C) IDENTIFICATION METHOD: analogy with a known sequence
    or a consensus sequence
  (D) OTHER INFORMATION:

(x) PUBLICATION INFORMATION:
  (A) AUTHORS:
  (B) TITLE:
  (C) JOURNAL:
  (D) VOLUME:
  (E) ISSUE:
  (F) PAGES:
  (G) DATE:
  (K) RELEVANT RESIDUES IN SEQ ID NO: 1: FROM 1 TO 1020

(xi) SEQUENCE DESCRIPTION: SEQ ID NO: 1:

| | | | | | | |
|---|---|---|---|---|---|---|
| TGTGGAGGTC AGAGTGGAAG CAGGTGTGAG AGGGTCCAGC AGAAGGAAAC ATG GCT | | | | | | 56 |
| | | | | | Met Ala | |
| | | | | | 1 | |

| GCC | AAA | GTG | TTT | GAG | TCC | ATT | GGC | AAG | TTT | GGC | CTG | GCC | TTA | GCT | GTT | 104 |
|---|---|---|---|---|---|---|---|---|---|---|---|---|---|---|---|---|
| Ala | Lys | Val | Phe | Glu | Ser | Ile | Gly | Lys | Phe | Gly | Leu | Ala | Leu | Ala | Val | |
| | 5 | | | | | 10 | | | | | | 15 | | | | |

| GCA | GGA | GGC | GTG | GTG | AAC | TCT | GCC | TTA | TAT | AAT | GTG | GAT | GCT | GGG | CAC | 152 |
|---|---|---|---|---|---|---|---|---|---|---|---|---|---|---|---|---|
| Ala | Gly | Gly | Val | Val | Asn | Ser | Ala | Leu | Tyr | Asn | Val | Asp | Ala | Gly | His | |
| 20 | | | | | 25 | | | | | | 30 | | | | | |

| AGA | GCT | GTC | ATC | TTT | GAC | CGA | TTC | CGT | GGA | GTG | CAG | GAC | ATT | GTG | GTA | 200 |
|---|---|---|---|---|---|---|---|---|---|---|---|---|---|---|---|---|
| Arg | Ala | Val | Ile | Phe | Asp | Arg | Phe | Arg | Gly | Val | Gln | Asp | Ile | Val | Val | |
| 35 | | | | 40 | | | | | 45 | | | | | 50 | | |

| GGG | GAA | GGG | ACT | CAT | TTT | CTC | ATC | CCG | TGG | GTA | CAG | AAA | CCA | ATT | ATC | 248 |
|---|---|---|---|---|---|---|---|---|---|---|---|---|---|---|---|---|
| Gly | Glu | Gly | Thr | His | Phe | Leu | Ile | Pro | Trp | Val | Gln | Lys | Pro | Ile | Ile | |
| | | | | 55 | | | | | 60 | | | | | 65 | | |

| TTT | GAC | TGC | CGT | TCT | CGA | CCA | CGT | AAT | GTG | CCA | GTC | ATC | ACT | GGT | AGC | 296 |
|---|---|---|---|---|---|---|---|---|---|---|---|---|---|---|---|---|
| Phe | Asp | Cys | Arg | Ser | Arg | Pro | Arg | Asn | Val | Pro | Val | Ile | Thr | Gly | Ser | |
| | | 70 | | | | | 75 | | | | | 80 | | | | |

| AAA | GAT | TTA | CAG | AAT | GTC | AAC | ATC | ACA | CTG | CGC | ATC | CTC | TTC | CGG | CCT | 344 |
|---|---|---|---|---|---|---|---|---|---|---|---|---|---|---|---|---|
| Lys | Asp | Leu | Gln | Asn | Val | Asn | Ile | Thr | Leu | Arg | Ile | Leu | Phe | Arg | Pro | |
| | | 85 | | | | | 90 | | | | | 95 | | | | |

| GTC | GCC | AGC | CAG | CTT | CCT | CGC | ATC | TTC | ACC | AGC | ATC | GGA | GAG | GAC | TAT | 392 |
|---|---|---|---|---|---|---|---|---|---|---|---|---|---|---|---|---|
| Val | Ala | Ser | Gln | Leu | Pro | Arg | Ile | Phe | Thr | Ser | Ile | Gly | Glu | Asp | Tyr | |
| | 100 | | | | 105 | | | | | 110 | | | | | | |

| GAT | GAG | CGT | GTG | CTG | CCG | TCC | ATC | ACA | ACT | GAG | ATC | CTC | AAG | TCA | GTG | 440 |
|---|---|---|---|---|---|---|---|---|---|---|---|---|---|---|---|---|
| Asp | Glu | Arg | Val | Leu | Pro | Ser | Ile | Thr | Thr | Glu | Ile | Leu | Lys | Ser | Val | |
| 115 | | | | | 120 | | | | | 125 | | | | | 130 | |

| GTG | GCT | CGC | TTT | GAT | GCT | GGA | GAA | CTA | ATC | ACC | CAG | AGA | GAG | CTG | GTC | 488 |
|---|---|---|---|---|---|---|---|---|---|---|---|---|---|---|---|---|
| Val | Ala | Arg | Phe | Asp | Ala | Gly | Glu | Leu | Ile | Thr | Gln | Arg | Glu | Leu | Val | |
| | | | | 135 | | | | | 140 | | | | | 145 | | |

| TCC | AGG | CAG | GTG | AGC | GAC | GAC | CTT | ACA | GAG | CGA | GCC | GCC | ACC | TTT | GGG | 536 |
|---|---|---|---|---|---|---|---|---|---|---|---|---|---|---|---|---|
| Ser | Arg | Gln | Val | Ser | Asp | Asp | Leu | Thr | Glu | Arg | Ala | Ala | Thr | Phe | Gly | |
| | | | 150 | | | | | 155 | | | | | 160 | | | |

| CTC | ATC | CTG | GAT | GAC | GTG | TCC | TTG | ACA | CAT | CTG | ACC | TTC | GGG | AAG | GAG | 584 |
|---|---|---|---|---|---|---|---|---|---|---|---|---|---|---|---|---|
| Leu | Ile | Leu | Asp | Asp | Val | Ser | Leu | Thr | His | Leu | Thr | Phe | Gly | Lys | Glu | |
| | | 165 | | | | | 170 | | | | | 175 | | | | |

| TTC | ACA | GAA | GCG | GTG | GAA | GCC | AAA | CAG | GTG | GCT | CAG | CAG | GAA | GCA | GAG | 632 |
|---|---|---|---|---|---|---|---|---|---|---|---|---|---|---|---|---|
| Phe | Thr | Glu | Ala | Val | Glu | Ala | Lys | Gln | Val | Ala | Gln | Gln | Glu | Ala | Glu | |
| | 180 | | | | | 185 | | | | | 190 | | | | | |

| AGG | GCC | AGA | TTT | GTG | GTG | GAA | AAG | GCT | GAG | CAA | CAG | AAA | AAG | GCC | GCC | 680 |

| | | | | | | | | | | | | | | | | |
|---|---|---|---|---|---|---|---|---|---|---|---|---|---|---|---|---|
| Arg<br>195 | Ala | Arg | Phe | Val | Val<br>200 | Glu | Lys | Ala | Glu<br>205 | Gln | Gln | Lys | Lys | Ala | Ala<br>210 | |
| ATC<br>Ile | ATC<br>Ile | TCT<br>Ser | GCT<br>Ala | GAG<br>Glu<br>215 | GGC<br>Gly | GAC<br>Asp | TCC<br>Ser | AAG<br>Lys | GCA<br>Ala<br>220 | GCT<br>Ala | GAG<br>Glu | CTG<br>Leu | ATT<br>Ile | GCC<br>Ala<br>225 | AAC<br>Asn | 728 |
| TCA<br>Ser | CTG<br>Leu | GCC<br>Ala | ACT<br>Thr<br>230 | GCA<br>Ala | GGG<br>Gly | GAT<br>Asp | GGC<br>Gly | CTG<br>Leu | ATC<br>Ile<br>235 | GAG<br>Glu | CTG<br>Leu | CGC<br>Arg | AAG<br>Lys<br>240 | CTG<br>Leu | GAA<br>Glu | 776 |
| GCT<br>Ala | GCA<br>Ala | GAG<br>Glu<br>245 | GAC<br>Asp | ATC<br>Ile | GCG<br>Ala | TAC<br>Tyr | CAG<br>Gln<br>250 | CTC<br>Leu | TCA<br>Ser | CGC<br>Arg | TCT<br>Ser | CGG<br>Arg<br>255 | AAC<br>Asn | ATC<br>Ile | ACC<br>Thr | 824 |
| TAC<br>Tyr | CTG<br>Leu<br>260 | CCA<br>Pro | GCG<br>Ala | GGG<br>Gly | CAG<br>Gln | TCC<br>Ser<br>265 | GTG<br>Val | CTC<br>Leu | CTC<br>Leu | CAG<br>Gln | CTG<br>Leu<br>270 | CCC<br>Pro | CAG<br>Gln | | | 866 |

TGAGGGCCCA CCCTGCCTGC ACCTCCGCGGG CTGACTGGG CCACAGCCCC GATGATTCTT    926

AACACAGCCT TCCTTCTGCT CCCACCCCAG AAATCACTGT GAAATTTCAT GATTGGCTTA    986

AAGTGAAGGA AATAAAGGTA AAATCACTTC AGAT    1020

(2) INFORMATION FOR SEQ ID NO: 2:

(i) SEQUENCE CHARACTERISTICS:
        (A) LENGTH: 850 base pairs
        (B) TYPE: nucleic acid
        (C) STRANDEDNESS: double
        (D) TOPOLOGY: linear (ii) MOLECULE TYPE: Genomic DNA (iii) HYPOTHETICAL: yes (iv) ANTI-SENSE: no (vi) ORIGINAL SOURCE:
        (A) ORGANISM: Homosapiens
        (C) INDIVIDUAL ISOLATE:
        (G) CELL TYPE:

(vii) IMMEDIATE SOURCE:
        (A) LIBRARY: human chromosome
        (B) CLONE:

(ix) FEATURE:
        (A) NAME/KEY: intron
        (B) LOCATION:
        (C) IDENTIFICATION METHOD: experimental
        (D) OTHER INFORMATION:

(ix) FEATURE:
        (A) NAME/KEY: exon
        (B) LOCATION:
        (C) IDENTIFICATION METHOD: experimental
        (D) OTHER INFORMATION:

(x) PUBLICATION INFORMATION:
        (A) AUTHORS:
        (B) TITLE:
        (C) JOURNAL:
        (D) VOLUME:
        (E) ISSUE:
        (F) PAGES:
        (G) DATE:
        (K) RELEVANT RESIDUES IN SEQ ID NO: 2: FROM 1 TO 850

(xi) SEQUENCE DESCRIPTION: SEQ ID NO: 2:

CCCTGTCTCT ACAAAACCAT CAAACAGCTG GGTGTGGCGG CGCGTGCTTG TAATCCCAGC    60

TACTCAGGAG GCTGAGGCAG GAGAATTGCT TGAATCTGGG AGGCAGAGGT TGTAGTGAGC    120

CCAGATTGTC CATGTACTCC AGCCTAGGCA ACAAGAGCAA AAACCTGTCT CAAAAAAAA    180

AAAAAACAAA AAAAAAACAC TTGTTTTCCT ACAGTGGTTT TTATTTTTAA CTCCAGTGTT    240

TGTCCCCTAC CCTAAGAT TTA CAG AAT GTC AAC ATC ACA CTG CGC ATC CTC    291

```
                    Leu  Gln  Asn  Val  Asn  Ile  Thr  Leu  Arg  Ile  Leu
                     85                  90                            95

TTC  CGG  CCT  GTC  GCC  AGC  CAG  CTT  CCT  CGC  ATC  TTC  ACC  AGC  ATC  GGA         339
Phe  Arg  Pro  Val  Ala  Ser  Gln  Leu  Pro  Arg  Ile  Phe  Thr  Ser  Ile  Gly
                    100                      105                      110

GAG  GAC  TAT  GAT  GAG  CGT  GTG  CTG  CCG  TCC  ATC  ACA  ACT  GAG  ATC  CTC         387
Glu  Asp  Tyr  Asp  Glu  Arg  Val  Leu  Pro  Ser  Ile  Thr  Thr  Glu  Ile  Leu
                    115                      120                      125

AAG  TCA  GTG  GTG  GTGAGTGAAC  AGGGGCCTTT  AGCTCGAGCC  CAGAGCACCA                      439
Lys  Ser  Val  Val
               130

CCCTGGGAGG  GGCGCAGGTG  GCAGGAAGCG  CTTGGCAGTG  GGTTGGTTGG  GATGTGGCTG                  499

CTAGTTTCCT  GGTTCCTTTT  CTGCTTCCTC  ATTAACCTGA  CCTGCCCTTC  TGCTCCTCCC                  559

TTTGAAACCA  G  GCT  CGC  TTT  GAT  GCT  GGA  GAA  CTA  ATC  ACC  CAG  AGA  GAG         609
               Ala  Arg  Phe  Asp  Ala  Gly  Glu  Leu  Ile  Thr  Gln  Arg  Glu
                              135                      140

CTG  GTC  TCC  AGG  CAG  GTG  AGC  GAC  GAC  CTT  ACA  GAG  CGA  GCC  GCC  ACC         657
Leu  Val  Ser  Arg  Gln  Val  Ser  Asp  Asp  Leu  Thr  Glu  Arg  Ala  Ala  Thr
145                      150                      155                      160

TTT  GGG  CTC  ATC  CTG  GAT  GAC  GTG  TCC  TGG  GTAAGATCCT  TCGGGAGACC               707
Phe  Gly  Leu  Ile  Leu  Asp  Asp  Val  Ser  Leu
                    165                      170

GAGGAGGGGG  AAGGGGCTGC  AGTTCTCGTT  TAGGTGCCTG  GCTCCATTCT  GGGTAGACGC                  767

TATTAGGTCC  TCCTTCTGCT  TGCTAGATGT  GAGACTTGAA  ACACGAACAT  CCTGAGGTGA                  827

GGCAGTTCCG  TGGTTCAGTG  AGG                                                             850
```

( 2 ) INFORMATION FOR SEQ ID NO: 3:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: other nucleic acid (synthetic DNA)

( x i ) SEQUENCE DESCRIPTION: SEQ ID NO: 3:

```
        TCACCCTCAG  CAGAGATGAT                                                          20
```

( 2 ) INFORMATION FOR SEQ ID NO: 4:

( i ) SEQUENCE CHARACTERISTICS:
        ( A ) LENGTH: 20 base pairs
        ( B ) TYPE: nucleic acid
        ( C ) STRANDEDNESS: single
        ( D ) TOPOLOGY: linear ( i i ) MOLECULE TYPE: other nucleic acid (synthetic DNA)

( x i ) SEQUENCE DESCRIPTION: SEQ ID NO: 4:

```
        CGCTCTCGAC  CACGTAATGT                                                          20
```

( 2 ) INFORMATION FOR SEQ ID NO: 5:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: other nucleic acid (synthetic DNA)

( x i ) SEQUENCE DESCRIPTION: SEQ ID NO: 5:

```
        TTAACAACTA  AGGGTATCGA  CAATG                                                   25
```

( 2 ) INFORMATION FOR SEQ ID NO: 6:

( i ) SEQUENCE CHARACTERISTICS:
        ( A ) LENGTH: 25 base pairs
        ( B ) TYPE: nucleic acid
        ( C ) STRANDEDNESS: single
        ( D ) TOPOLOGY: linear ( i i ) MOLECULE TYPE: other nucleic acid (synthetic DNA)

( x i ) SEQUENCE DESCRIPTION: SEQ ID NO: 6:

```
AATTGTTGAT TCCCATAGCT GTTAC                              25
```

( 2 ) INFORMATION FOR SEQ ID NO: 7:

( i ) SEQUENCE CHARACTERISTICS:
        ( A ) LENGTH: 14 base pairs
        ( B ) TYPE: nucleic acid
        ( C ) STRANDEDNESS: single
        ( D ) TOPOLOGY: linear ( i i ) MOLECULE TYPE: Genomic DNA ( v i ) ORIGINAL SOURCE:
        ( A ) ORGANISM: Homosapiens
        ( G ) CELL TYPE: breast cancer cell ( i x ) FEATURE:
        ( A ) NAME/KEY: mutation
        ( C ) IDENTIFICATION METHOD: experimentation ( x i ) SEQUENCE DESCRIPTION: SEQ ID NO: 7:

```
GTG gtgagtgaat a                                          14
```

( 2 ) INFORMATION FOR SEQ ID NO: 8:

( i ) SEQUENCE CHARACTERISTICS:
        ( A ) LENGTH: 31 base pairs
        ( B ) TYPE: nucleic acid
        ( C ) STRANDEDNESS: double
        ( D ) TOPOLOGY: linear ( i i ) MOLECULE TYPE: other nucleic acid (synthetic DNA)

( x i ) SEQUENCE DESCRIPTION: SEQ ID NO: 8:

```
AGCCCGCCTA ATGAGCGGGC TTTTTTTCA G                         31
```